United States Patent [19]
Cowan et al.

[11] Patent Number: 5,983,129
[45] Date of Patent: Nov. 9, 1999

[54] METHOD FOR DETERMINING AN INDIVIDUAL'S INTENSITY OF FOCUSED ATTENTION AND INTEGRATING SAME INTO COMPUTER PROGRAM

[76] Inventors: Jonathan D. Cowan, 1103 Hollendale, Goshen, Ky. 40026; Andrew J. Prell, 7341 Saint Andrews Church Rd., Apartment 6, Louisville, Ky. 40214

[21] Appl. No.: 09/026,324

[22] Filed: Feb. 19, 1998

[51] Int. Cl.⁶ .................................................. A61B 5/04
[52] U.S. Cl. ........................ 600/544; 600/545; 600/558; 128/905
[58] Field of Search ................................... 600/544, 545, 600/558; 128/905

[56] References Cited

U.S. PATENT DOCUMENTS

| | | | |
|---|---|---|---|
| 3,490,439 | 1/1970 | Rolston | 128/2.1 |
| 3,508,541 | 4/1970 | Westbrook et al. | 128/2.1 |
| 3,978,847 | 9/1976 | Fehmi et al. | 128/2.1 B |
| 3,998,213 | 12/1976 | Price | 128/2.1 B |
| 4,031,883 | 6/1977 | Fehmi et al. | 128/2.1 B |
| 4,033,334 | 7/1977 | Fletcher et al. | 128/2.1 E |
| 4,149,716 | 4/1979 | Scudder | 273/1 E |
| 4,311,152 | 1/1982 | Modes et al. | 128/641 |
| 4,537,198 | 8/1985 | Corbett | 128/639 |
| 4,955,388 | 9/1990 | Silberstein | 600/545 |
| 5,038,782 | 8/1991 | Gevins et al. | 128/644 |
| 5,209,494 | 5/1993 | Spector | 273/460 |
| 5,273,037 | 12/1993 | Itil et al. | 128/644 |
| 5,280,793 | 1/1994 | Rosenfeld | 128/732 |
| 5,295,491 | 3/1994 | Gevins | 128/731 |
| 5,304,112 | 4/1994 | Mrklas et al. | 600/27 |
| 5,306,228 | 4/1994 | Rubins | 600/27 |
| 5,348,006 | 9/1994 | Tucker | 128/639 |
| 5,357,957 | 10/1994 | Itil et al. | 128/644 |
| 5,377,100 | 12/1994 | Pope et al. | 364/410 |
| 5,406,957 | 4/1995 | Tansey | 128/732 |
| 5,409,445 | 4/1995 | Rubins | 600/27 |
| 5,450,855 | 9/1995 | Rosenfeld | 128/732 |
| 5,571,057 | 11/1996 | Ayers | 463/36 |
| 5,601,091 | 2/1997 | Dolphin | 128/746 |
| 5,645,063 | 7/1997 | Straka, Jr. | 128/641 |
| 5,662,117 | 9/1997 | Bittman | 128/732 |
| 5,724,987 | 3/1998 | Gevins et al. | 600/544 |
| 5,762,611 | 6/1998 | Lewis et al. | 600/544 |

FOREIGN PATENT DOCUMENTS 0177075  4/1986  European Pat. Off. .

*Primary Examiner*—Cary O'Connor
*Assistant Examiner*—Navin Natnithithadha
*Attorney, Agent, or Firm*—Middleton & Reutlinger

[57] ABSTRACT

A method for determining an individual's intensity of focused attention, comprising the steps of: obtaining a representative frontal lobe brainwave signal from at least one first sensor in an electrically connective relation to the individual's frontal lobe; obtaining a representative reference signal from at least one second sensor in an electrically connective relation to a more electrically-neutral location; subtracting the representative reference signal from the representative frontal lobe brainwave signal to produce a difference frontal lobe brainwave signal, and processing the difference frontal lobe brainwave signal to produce an Attention Indicator signal indicative of the individual's intensity of focused attention, where the Attention Indicator signal is inversely proportional to any mathematical transformation of an amplitude measure of the difference frontal lobe brainwave signal; inputting the Attention Indicator signal to a device; and, repeating these steps, as desired. The mathematical transformation can relate to amplitude, power or any linear, logarithmic or exponential transformation thereof.

32 Claims, 7 Drawing Sheets

METHOD FOR DETERMINING AN INDIVIDUAL'S INTENSITY OF FOCUSED ATTENTION AND INTEGRATING SAME INTO COMPUTER PROGRAM

BACKGROUND OF THE INVENTION

1. Technical Field of the Invention

The present invention relates to methods for determining an individual's intensity of focused attention, concentration and/or interest by measuring at least one signal emitted from the individual's body, such as, for example, from the individual's head, and generally from the frontal lobe of the brain. More particularly, the present invention relates to a method for determining an individual's intensity of focused attention by measuring at least one signal emitted from the individual's body wherein the signal emitted therefrom is processed and integrated as an attention indicator into a computer program, such as a video game, so that additional input is provided thereby. Even more particularly, the present invention relates to a new method for detecting a user's concentration, interest, and/or single-pointed focus of attention.

2. Discussion of the Prior Art

The brain produces electrical signals from at least 0–40 Hertz ("Hz"), which are measurable from the scalp. These signals constitute the EEG or electroencephalogram. All the previous patents and inventions related to EEG have been based upon an intellectual framework that specified that signals from about 0–4 Hz often indicate a deep sleep state (the so-called, "delta" range); signals from about 4–8 Hz indicate a reverie or daydreaming state (the so-called, "theta" range); signals from about 8–13 Hz indicate an alert, but less mentally busy state (the so-called, "alpha" range); and, signals above 13 Hz indicate a vigilant state (the so-called, "beta" range).

While this may be true of signals measured from a majority of the cortex, this invention is based on the first applicant's research, which indicates that an additional phenomenon can be reliably demonstrated in the frontal and fronto-central midline portions of the brain surrounding the sites labeled FCz, Fz, AFz and FPz by electroencephalographers. In these areas, which overlie portions of the Executive Attention Network, attention focused on an object causes all of these organized brainwave patterns to diminish in intensity. They are presumably replaced by a higher frequency, very random cortical activation pattern that would be very difficult to measure with a traditional EEG instrument, since they are attenuated by the skull. The present invention monitors focused attention, concentration, and interest by measuring the decrease of organized EEG output from 0–40 Hz at one or more of these sites. The largest decrease in amplitude or power while focusing generally takes place between 0–11 Hz. To Applicants' knowledge, no prior teaching has set forth a method in which the inhibition of frontal lobe EEG signals has been used to provide an attention indicator.

It is desirable to provide a method to detect this decrease in brainwave output and to integrate the signal into a computer program, such as a video game.

It is even further desirable to provide a method to detect a signal produced from an individual's brain and to derive therefrom a measure of the individual's intensity of focused attention, level of concentration or interest in a particular experience.

For example, U.S. Pat. No. 5,571,057 to Ayers teaches an apparatus and method for selecting prearranged sequences of visual images in response to a bioelectrical signal emitted from a portion of a user's body, such as, for example, from the user's head. However, it is also desirable to provide a method to detect a signal produced by an individual's brain and to integrate the signal detected thereby into a computer program, such as a video game, with or without images, such that the additional input provided thereby affects, influences, adjusts and modifies operation of the computer program, such as a video game, in a complex and customizable fashion.

For example, European Patent Application No. 177,075 to Ugo, et al., sketchily teaches an electronic system for use with an electronic game, wherein existing manual controls manipulable by a user's hands are entirely replaced with equivalent controls manipulable directly by signals emitted from the user's brain. However, it is further desirable to provide a method to detect signals produced by an individual's brain, preferably with a single EEG sensor placed in the midline location described above, and to process these signals by a method that responds and/or adapts to the user's degree of concentration, interest, and/or one-pointed focus of attention. It is furthermore desirable to provide a method of processing and integrating the signal detected thereby into a computer program, such as a video game, wherein the manual control, such as, for example, by a joystick, keyboard, mouse or other similar input device, of the computer program, such as a video game, is enabled or supplemented, but not totally replaced, by complex control inputs derived from the signal detected thereby. Furthermore, based on the attention indicator of the user, the logic driving the game can be modified.

SUMMARY OF THE INVENTION

The present invention is a method of detecting and processing an EEG signal that responds to the user's degree of concentration, interest and/or single-pointed focus of attention into a computer program, such as a video game. For example, many computer programs, such as video game or edutainment systems ("edutainment" is the combination of education and entertainment), include one or more input devices, such as, for example, a joystick, keyboard, mouse or other similar input device, to control and affect operation thereof in accomplishing the objective of the particular game program being played. As a further example, many computer programs, such as video games, place the individual player into a virtual world by creating a virtual character, whose actions the player controls through manipulation of the several input devices attached to the computer, such as a video game system, as though the player were actually in the virtual world himself. The player then controls the actions of the character to meet the primary objective of the computer program, such as, for example, to unravel the mysteries of a secret universe or to defeat a virtual enemy.

The present invention provides a method by which a user may more seamlessly integrate his mental focus and intentions into the virtual world presented by a computer program, such as a video game or edutainment program. For example, the present invention provides a headband or headset to be worn by the player, wherein sensors on the headband or headset detect measurable raw signals emitted from the player's head, and more particularly, from the player's brain, within a predetermined range of frequencies corresponding to the player's intensity of focused attention.

The preferred location for detecting a signal emitted from an individual's body is from the frontal or fronto-central midline portion of the individual's brain at or near locations on the individual's head typically referred to as FCz, Fz, AFz and FPz, where concentration or single-pointed focus of attention on an object by the individual causes organized brainwave patterns to diminish in intensity. In general, detection of the desired signal can occur within an area bounded by two lines, each running between the two earlobes, one passing through the shallowest portion of the nose (the nasion) and one passing through a point one inch forward of the highest, most central part of the head (the vertex). The present invention determines the intensity of focused attention, and the individual's interest indicated thereby, on an object upon which the individual is focusing, by measuring the decrease of organized EEG output from 0–40 Hz at the aforementioned locations. It is observed that the largest decrease in intensity occurs within the 0–11 Hz frequency band.

A headband sensor detects the raw signal being emitted by the player in response to the player's level of attention. The raw signal is converted by an interface unit into a functional Attention Indicator, which is then exported into the computer program, such as a video game system, to enable or supplement the existing manual controls which are manipulable by the player.

The functional Attention Indicator can be integrated into the computer program, such as a video game or edutainment program, to provide any manner of control thereto in response to the player's level of concentration, relaxation (defined herein as the opposite of concentration) or interest. In this manner, the present invention may be used to develop coordination between the eye, the brain, and the hand. For example, where a player's objective is to move an object under his control until it "catches" another object controlled and moved elusively by the computer program, such as a video game program, the brightness or clarity of the player's measured object may become less intense as the player loses concentration on it. Only when the player is concentrating sufficiently on his object will his object appear with sufficient resolution in order to permit him to control it as required by the game objective. Alternatively, the individual's concentration may be required to be of a sufficient intensity before the manual control of an aspect of the game, such as by a slider or button on a joystick or mouse, is enabled. As a further example, a predetermined threshold level, or a rapid increase in the player's level of concentration may be used to trigger a predetermined game event, such as, for example, the firing of a virtual gun. Furthermore, as the player focuses more intensely, the speed of his game object may increase, although so the object is still steered manually.

It is an object of the present invention to provide a method for detecting an EEG signal emitted from a portion of an individual's body, such as, for example, from the individual's head, and for deriving therefrom an Attention Indicator signal, that being an indication of the individual's concentration, relaxation or interest.

It is another object of the present invention to provide a method for detecting, processing and integrating a signal emitted from a portion of the individual's body, such as, for example, from the individual's head, into a computer program, such as a video game, wherein the additional input provided thereby affects operation of the computer program, such as a video game.

It is still another object of the present invention to provide a method for detecting, processing and integrating a signal emitted from a portion of the individual's body, such as, for example, from the individual's head, into a computer program, such as a video game or edutainment program, wherein manual controls, such as, for example, a joystick, keyboard, mouse or other similar input device, of the computer program, such as a video game, are not replaced, but are enabled or supplemented by control inputs derived from the signal detected by the apparatus.

It is yet another object of the present invention to provide a method for detecting, processing and integrating a signal emitted from a portion of the individual's body, such as, for example, from the individual's head, into a computer program, such as a video game or edutainment program, wherein the signal detected thereby is from an individual's brain, and wherein the signal is detected by single or multiple EEG sensors placed at or near a midline frontal or fronto-central region of the individual's head.

It is still a further object of the present invention to provide a method for detecting, processing and integrating a signal emitted from a portion of the individual's body, such as, for example, from the individual's head, wherein the signal detected thereby is used to assist the individual improve his concentration, as well as his ability to cycle between a more and a less focused state.

It is another object of the present invention to provide a method for monitoring and recording an individual's degree of attention, concentration or interest as he participates in or passively experiences events such as classes, movies, advertisements, video games, or sports events by inputting these brainwave concentration signals into a computer program.

It is still another object of the present invention to use this brainwave attention indicator as biofeedback to help the user to train and thereby improve his concentration and his ability to cycle between intense concentration and a more relaxed state. Furthermore, this invention also comprises the use of verbal instruction to help the user to transfer his focus of attention to other sensory inputs and/or mental experiences or various study or work tasks. It also comprises the audio-visual presentation of biofeedback information to the user as he is simultaneously performing other tasks, particularly in a Windows computer environment, in order to improve the user's performance, learning and retention of the task. A biofeedback protocol that is silent when the user is concentrating, but gently reminds the user to concentrate by emitting pleasant sounds when the brainwave Attention Indicator moves above a certain threshold, thereby indicating inattention, is one type that can be used for this purpose. However, other protocols which encourage concentration on simultaneously-occurring events by employing the functional Attention Indicator are also envisioned by this invention.

Even more specifically, the present invention includes a method for determining an individual's intensity of focused attention, comprising the steps of: obtaining a representative frontal lobe brainwave signal from at least one first sensor in an electrically connective relation to the individual's frontal lobe; obtaining a representative reference signal from at least one second sensor in an electrically connective relation to a more electrically-neutral location; subtracting the representative reference signal from the representative frontal lobe brainwave signal to produce a difference frontal lobe brainwave signal, and processing the difference frontal lobe brainwave signal to produce AIndicator signal indicative of the individual's intensity of focused attention, where the AIndicator signal is inversely proportional to any mathematical transformation of an amplitude measure of the difference frontal lobe brainwave signal; inputting the AIndicator signal to a device; and, repeating these steps, as desired. The mathematical transformation can relate to amplitude, power or any linear, logarithmic or exponential transformation thereof. The inverse relationship can be obtained by a number of mathematical means, including, but not limited to, (1) subtracting the mathematical transformation from any fixed number, or (2) dividing a fixed number by the mathematical transformation.

Even further, it is an object of this invention to monitor the Attention Indicator and therefrom to record and retain player preferences for later use in the video game or for the developer's use in later modification of the game and/or creation of future games. This invention can also be used to record, retain, and subsequently analyze and compare the degree of interest of users who are undergoing certain experiences, such as watching movies or advertisements, using educational materials, or participating in seminars or classes. Also, as part of the game's artificial intelligence, the Attention Indicator for presented events is monitored so that future events presented can be changed based upon the specific player or "type" of player.

BRIEF DESCRIPTION OF THE DRAWINGS

A better understanding of the present invention will be had upon reference to the following description in conjunction with the accompanying drawings in which like numerals refer to like parts, and wherein.

DETAILED DESCRIPTION OF THE PREFERRED EMBODIMENT

Figure 1:
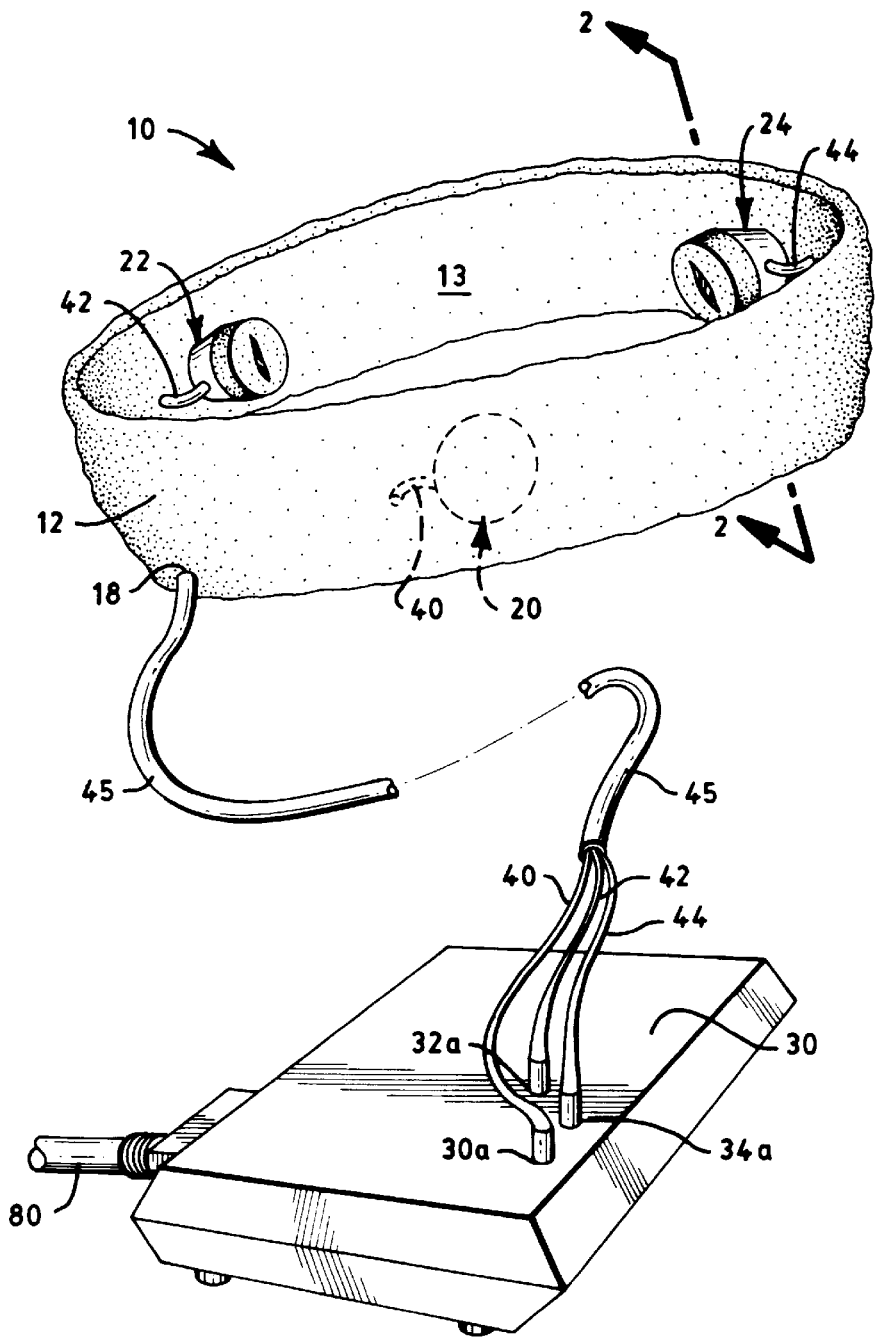
FIG. 1 is a perspective view of a headband according to the present invention shown connected to a signal-processing unit.

With reference to FIG. 1, a headband 10 according to a preferred embodiment of the present invention, and for use in detecting a signal emitted from an individual's body, such as, for example, from the individual's head, includes an elastic band member 12, a frontal lobe (or forehead) sensor unit 24 and a pair of ear-sensor units 20, 22 (sensor unit 20 being shown in phantom). The frontal lobe sensor unit 24 is fixedly attached to an inside surface 13 of the band member 12, such as, for example, by Lexel as hereinbelow described. The ear sensor units 20, 22 are fixedly attached to the inside surface 13 of the band member 12 as hereinbelow described. Alternatively, the frontal lobe sensor unit 24 (as shown in the Figures) and the ear sensor units 20, 22 may be removably attached to the band member 12, such as, for example, by hook-and-loop-type fastener 14. The band member 12 is constructed from any suitable elastic woven material with longitudinal stretch.

The frontal lobe sensor unit 24 and the ear sensor units 20, 22 are in electrical cooperative engagement with an interface unit 30 such that the interface unit 30 receives an "active" signal (a frontal lobe brainwave signal) from the frontal lobe sensor unit 24, a "ground" signal from the first ear sensor unit 20 and a "reference" signal from the second ear sensor unit 22. The sensor units 20, 22, 24 are electrically connected to the interface unit 30 by a 3-lead, shielded cable 45 wherein one lead 44 provided therein is electrically connected to the frontal lobe sensor unit 24, a second lead 40 provided therein is electrically connected to the first ear sensor unit 20 and a third lead 42 provided therein is electrically connected to the second ear sensor unit 22. The sensor units 20, 22, 24 by and through their respective leads 40, 42, 44 cooperate to provide a raw signal to the interface unit 30 representing an unfiltered, unprocessed electroencephalograph ("EEG") signal being emitted from an individual's head to which the headband 10 has been affixed as hereinafter described. Alternatively, the reference signal may be obtained by shorting, "linking" or "pooling" the signals from sensor units 20 and 22, and a ground signal may be obtained from any other part of the user's scalp or body by any connection means. The interface unit 30 is electronically connected to a computer system 90 (FIG. 4), by a cable 80 of a type necessary to properly connect to the computer system 90 according to the particular type of connection being thereby made, such as, for example, by connecting to either the serial port, the parallel port or an auxiliary joystick port of a computer or similar inputs depending on the particular system. It is noted that the term "computer" as used throughout this application, including the claims, is a broad general term for any system which receives input and executes a computer program. "Computer" includes the common "PC" in all varieties including a laptop, a desk top, a portable, or hand-held computer capable of running multiple of single function programs, arcade video games, home console video games, or a hand-held game such as produced by Sega and Nintendo, virtual reality games, and artificial intelligence systems. Also, "computer" could mean a plurality of computers. For example, two users with individual computers could be connected directly or by an INTERNET computer, for example. Each individual's computer could provide an Attention Indicator for that individual to one of the computers which could then use that indicator to vary what is presented to that or both individuals. Even further, a "computer" may include a device which functions to record or store information and/or events.

Figure 2:
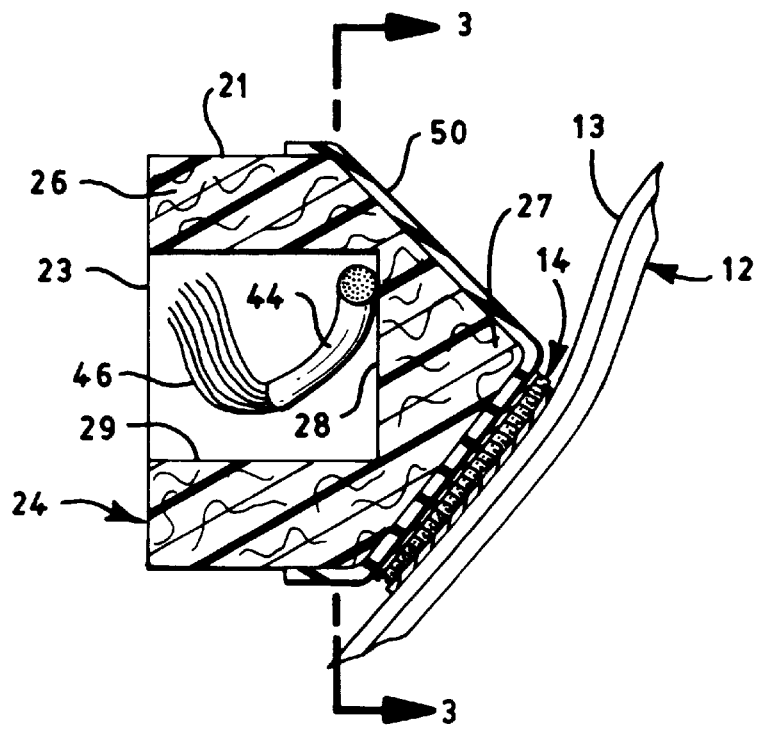
FIG. 2 is a side sectional view of a first sensor provided on the headband of FIG. 1 and shown along section lines 2—2 of FIG. 1.

With additional reference to FIG. 2, the forehead sensor unit 24 includes a sponge 26 having a substantially cylindrical shape tapered at one end 27 thereof from an outer periphery 21 thereof, along substantially flat upper and lower surfaces defined by the taper, to a substantially flat linear edge. The tapered end 27 of the sponge 26 is coated with an electrically-insulated, highly flexible, liquid-impermeable material 50, such as, for example, Lexel, which is comfortable to the user. The tapered shape reduces the tendency of the headband 10 to "roll over", thereby losing the connection to the user. The frontal lobe sensor unit 24 is fixedly attached to the inside surface 13 of the band member 12 by first coating one end of the respective sponge with a liquid-impermeable material 50, such as, for example, Lexel, permitting the liquid-impermeable material 50 to dry, coating the end of the sponge with the liquid-impermeable material 50 a second time, applying the end of the respective sponge to the inside surface 13 of the band member 12 and permitting the liquid-impermeable material 50 to dry. Either one, or preferably both, of substantially flat upper and lower surfaces of end 27 are fixedly attached to inside surface 13. Sufficient pressure is applied to the sponge while the liquid-impermeable material 50 is drying to permit the woven fibers of the band member 12 to be set within the hardened liquid-impermeable material 50. Alternatively, the frontal lobe sensor unit 24 may be removably attached to the inside surface 13 of the band member 12, such as, for example, by a hook-and-loop-type fastener 14, bonded by Lexel to both surfaces 50 and 13.

The ear sensor units 20, 22 each include a sponge having a substantially cylindrical or tapered shape which is coated with the liquid-impermeable material 50. The ear sensor units 20, 22 are fixedly attached to the inside surface 13 of the band member 12 by first coating one end of the respective sponge with the liquid-impermeable material 50, permitting the liquid-impermeable material 50 to dry, coating the end of the sponge with the liquid-impermeable material 50 a second time, applying the end of the respective sponge to the inside surface 13 of the band member 12 and permitting the liquid-impermeable material 50 to dry. Sufficient pressure is applied to the sponge while the liquid-impermeable material 50 is drying to permit the woven fibers of the band member 12 to be set within the hardened liquid-impermeable material 50. Construction of the ear sensor units 20, 22 is similar to construction of the forehead sensor unit 24 in all other respects and discussion of the forehead sensor unit 24 is intended to be illustrative of the ear sensor units 20, 22. This includes the discussion of the alternative hook and loop fastener 14.

An additional approach to affixing these sensor in close proximity to the requisite points on the scalp and ears can be constructed by mounting the three electrodes on a headphone, as described in detail in Cowan's co-pending U.S. patent application Ser. No. 08/590,405, incorporated herein by reference. The frontal lobe sensor can be mounted on the flexible metal extender that is riveted to the top of the headphone band. The two ear sensors can be mounted on the ear cups of the headphone. Mounting can be accomplished by Lexel or a similar compound, with or without a hook and loop fastener.

Figure 3:
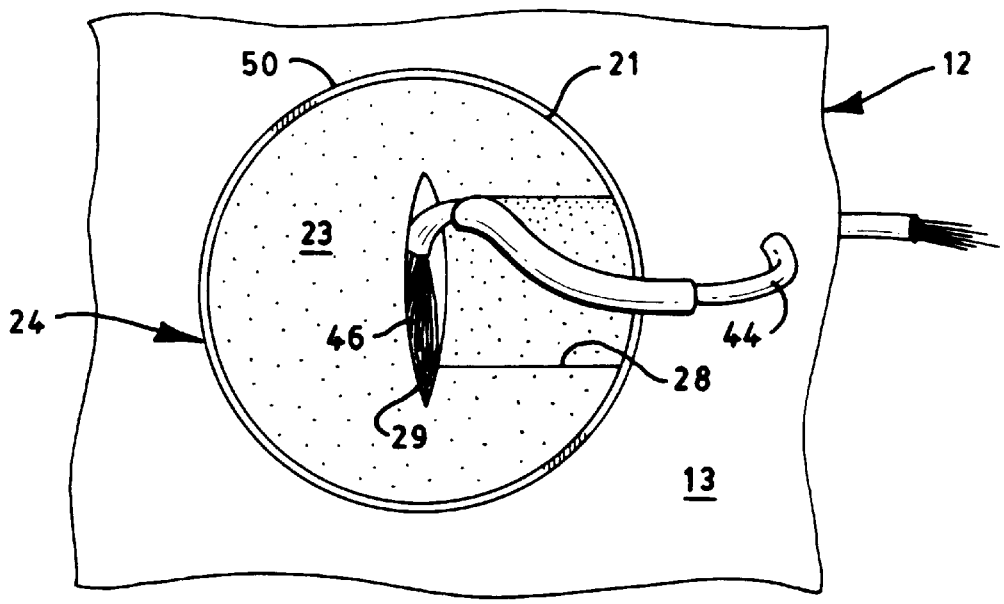
FIG. 3 is a front sectional view of the first sensor of FIG. 2 shown along section lines 3—3 of FIG. 2.

With additional reference to FIG. 3, a transverse slit 28 is provided partially through the sponge 26 between the outer periphery 21 thereof and a center portion thereof towards a longitudinal center region of the sponge. The transverse slit 28 communicates with a longitudinal slit 29 provided partially through the sponge 26 between the transverse slit 28 and an inner face 23 of the sponge 26 opposite the tapered end 27 thereof.

The second lead 44 projects into the transverse slit 28 and is frictionally secured within the sponge 26 between opposing interior faces being defined by the longitudinal slit 29. A plurality of conductive wires 46 provided within the second lead 44 extend therefrom and are frayed and balled up sufficiently to create an electrical connection to the scalp through a conductive solution, within the longitudinal slit 29 towards the inner face 23 of the sponge 26. Although an EEG electrode could be connected to the second lead 44, corrosion-resistant fraying wires 46, such as, for example, of stainless steel, have been shown to satisfactorily detect the brainwave signals. The liquid-impermeable material 50 adheres the second lead 44 to the sponge 26, thereby reducing a tendency of the lead 44 to become disassociated therefrom.

With reference back to FIG. 1, the leads 40, 42, 44 extend from their respective sensor units 20, 22, 24, through the band member 12 and exit the band member 12 from a single location, denoted generally as reference numeral 18. An outer sleeve of the cable 45 is removed therefrom so that the leads 40, 42, 44 are permitted to diverge therefrom within the band member 12.

Figure 4:
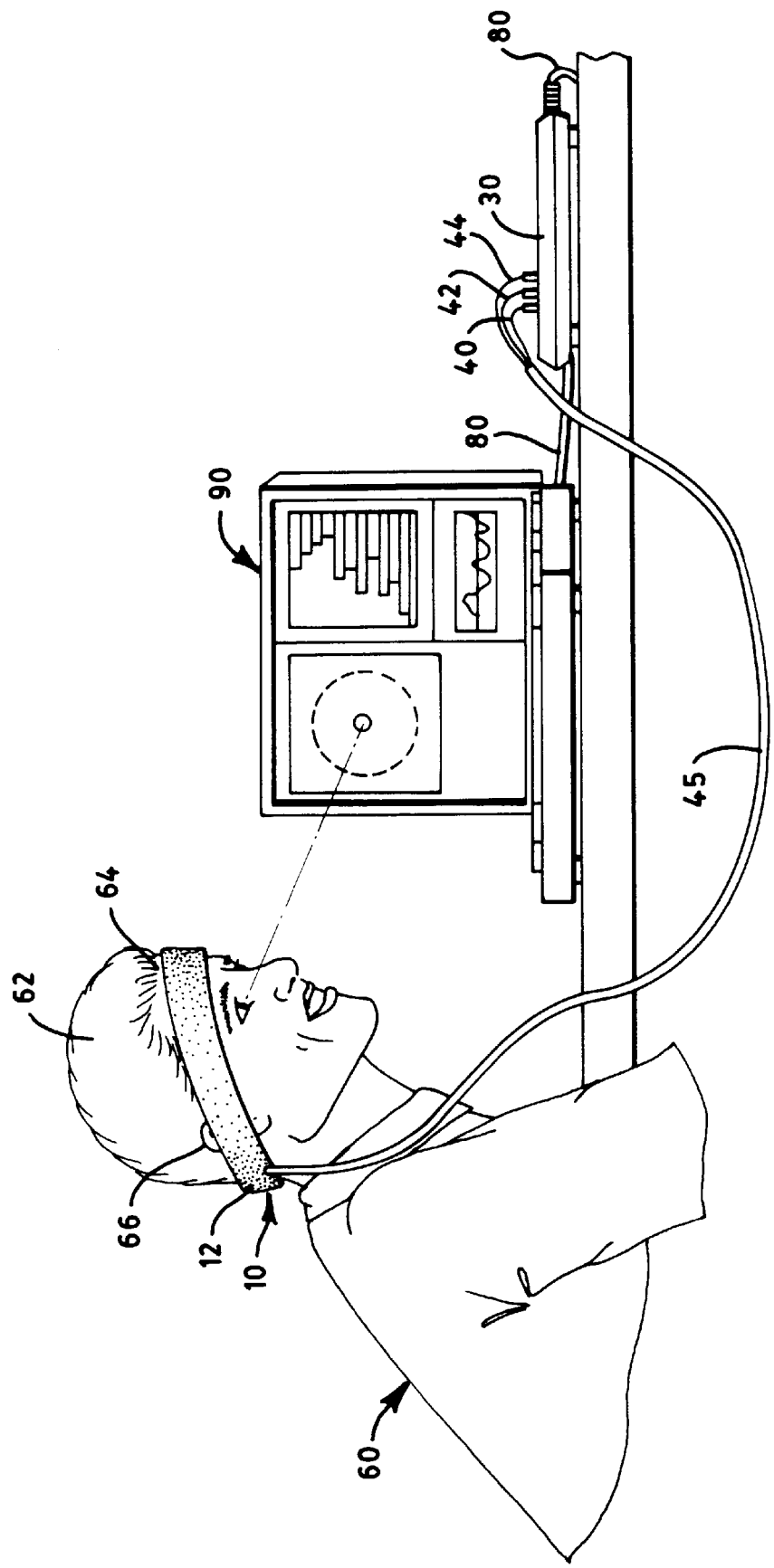
FIG. 4 is a side view of the headband of FIG. 1 shown being worn by a user thereof and in operative relationship with a computer program, such as a video game or edutainment system.

With reference to FIG. 4, a user 60 places the headband 10 around his head 62 so that the frontal lobe sensor unit 24 rests firmly against the user's forehead 64, and that the ear sensor units 20, 22 rest against respective upper portions of the user's ears 66 (only one being shown). The frontal lobe sensor unit 20 is preferably positioned to detect signals from the AFz location, that being approximately at the midline of the head, just below the hairline. However, it can be located in many locations overlying the frontal lobe, within an area bounded by two lines, each running between the two earlobes, one passing through the shallowest portion of the nose (the nasion) and one passing through a point one inch forward of the highest, most central part of the head (the vertex). Each sensor unit is soaked and squeezed several times in a conductive solution, such as, for example, salt water, or a small amount of this conductive solution is deposited within each longitudinal slit 29 of the sensor units 20, 22, 24 prior to the user's placing the headband 10 upon his head. The conductive solution ensures an electrical connection between the frayed end portion 46 of the leads 40, 42, 44 and the user's forehead 64. The coating 50 retains the conductive solution within the sponge 26 and prevents accelerated drying thereof, while maintaining maximum user comfort. The leads 40, 42, 44 are connected to corresponding plugs 30a, 32a, 34a provided on the interface unit 30, which is connected by a cable 80 to the computer or video game system 90, as hereinabove described. Alternatively, a single connector with three wires may be used.

Figure 5:
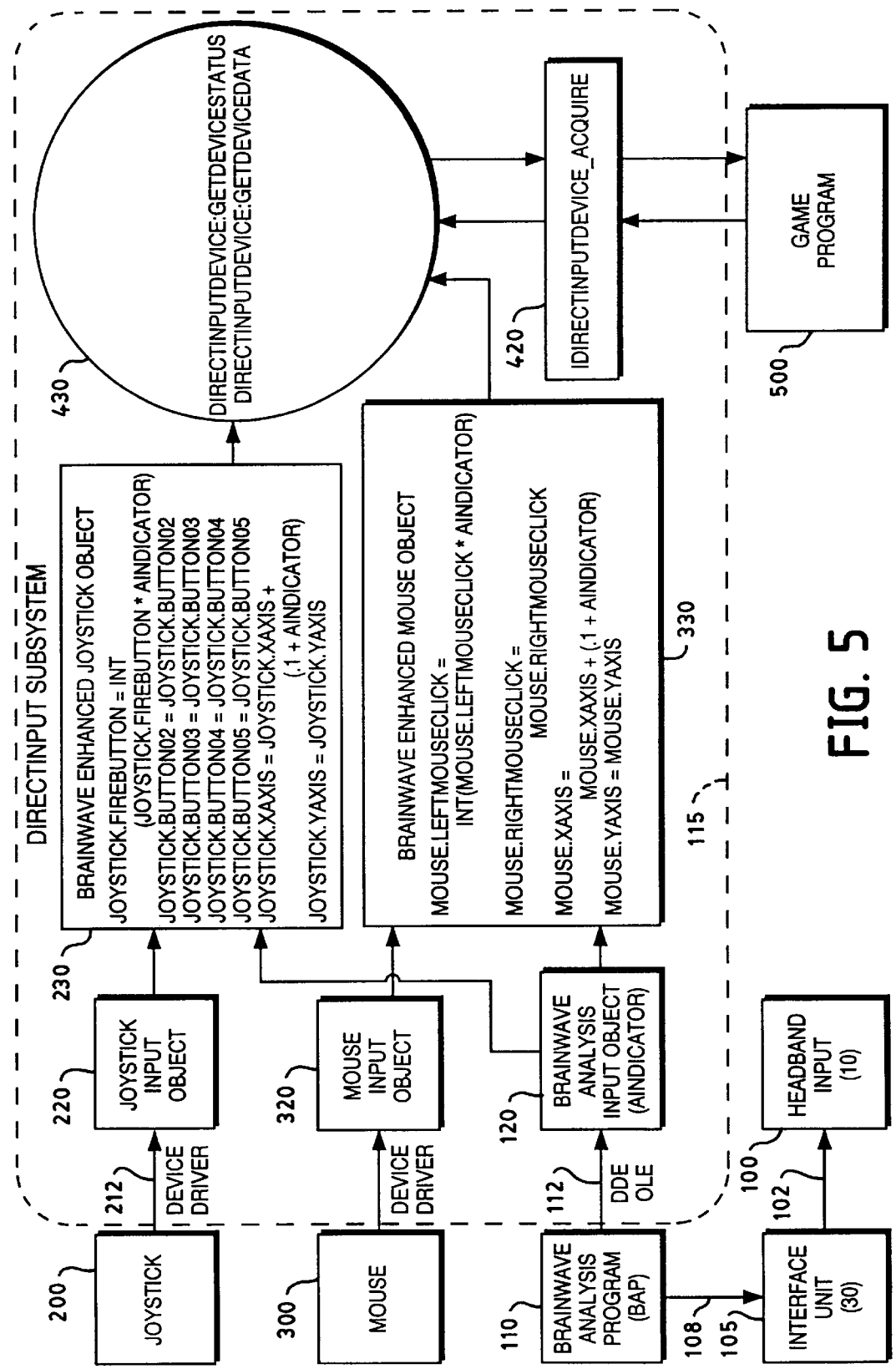
FIG. 5 is a flow chart representation showing how the Attention Indicator signal can be used to affect joystick and mouse inputs.

With reference to FIG. 5, there is shown a method for integrating a raw signal input 100 detected by the headband 10 (FIG. 1) as hereinabove described into a computer program, such as a video game program 500, wherein a user's operation thereof is enhanced by supplementing existing manual controls, such as, for example, joystick input 200 and/or mouse input 300 with the headband input 100. As seen in FIG. 5, the Attention Indicator signal (or "AIndicator") from 120 is being used to affect the joystick fire button, the joystick XAxis, the mouse left click button, and the mouse XAxis. This is only an example and any one or any combination of inputs could be affected by the Attention Indicator.

Alternatively, or in addition, the Attention Indicator can be used to directly modify program variables. For example, with increased concentration, the damage produced by the player could be increased or the damage taken by the player could be decreased. For example, a player concentrating at one level could incur less damage when "breaking" a laser beam than a player concentrating at a lesser level. Also, the game scoring values could be increased or decreased depending on the Attention Indicator value.

The raw signal 102 detected by the headband 10 sensors 20, 22, 24 is amplified, digitized and filtered by the interface unit 30 to provide a processed signal 108 of between 0–40 Hz, a value of which, such as the cumulative power or amplitude thereof, is then exported to a brainwave analysis program ("BAP") 110 running on a computer, wherein the brainwave analysis computer may be separated from the main computer, such as a video game system 90, or may be a software subset or other subroutine thereof. The BAP 110 derives a particular intensity of attention 112 from the processed signal 108 being received thereby by measuring and processing the total strength of the processed signal 108 at all frequencies within the 0–40 Hz band. As the total strength of the processed signal 108 decreases, the intensity of concentration, interest, and/or focused attention increases. To facilitate the user's comprehension of his attention intensity, the Attention Indicator may be averaged over a desired time interval.

The correlated concentration/interest level signal is called the Attention Indicator signal. Deliberate or non-deliberate attention can affect the Attention Indicator (or AIndicator) signal. For example, the player can increase the AIndicator by forced or deliberate concentration. Alternatively, the AIndicator may increase simply as a result of the intrigue of the game being played, a non-deliberate increase caused by the player becoming interested in what he is doing at the time and therefore focusing on it more intensely.

The raw signal 102 received by the BAP may be made more reliable by eliminating sudden changes therein due to external influences, such as, for example, due to sudden eye or head movement. The interface unit 30 may include a digital filter, or any equivalent time-averaging means of filtering thereto, to remove sudden increases or decreases in signal strength.

Alternatively, the interface unit 30 may provide a processed signal 108 to the BAP 110 of a range between any two values within the broad 1–40 Hz range, such as, for example, between 2–11 Hz. In this manner, the method described herein may focus on a specific type of attention, which will then be integrated into the game program 500.

The BAP 110 creates an output, the Attention Indicator 112, which increases with increased concentration, interest, or focused attention, within the desired range, for example from 0 to 10. The Attention Indicator may be modified in response to a user-specified difficulty parameter, or in response to automated modification thereof by the BAP 110, which may adjust it by comparing it to the user's past performance.

The BAP output 112 is exported via data transport protocols, such as, for example, so-called Dynamic Data Exchange ("DDE") protocol or so-called Object Linking and Embedding ("OLE") protocol, to the Game Program Direct-Input Subsystem ("GPDIS") 115 of the game program 500, which utilizes Microsoft's trademarked DirectX and Direct-Input data exchange protocols to receive and integrate input from numerous input devices, such as a joystick or mouse, which the GPDIS acquires through conventional device drivers.

More particularly, as shown, the GPDIS 115 is programmed to into include a Brainwave Enhanced Joystick Object 230 or Brainwave Enhanced Mouse Object 330 for each of the input devices. For instance, where the game program 500 requires input only from the joystick, the GPDIS 115 creates an enhanced object instance 230 corresponding thereto. Similarly, where the game program 500 requires input only from the mouse, the GPDIS 115 creates an enhanced object instance 330 corresponding thereto. In many computer programs, such as video game programs, input may be required from more than one joystick or mouse; for such a case, the GPDIS 115 creates a number of instances corresponding to each. In each case the objects can be configured or customized to properly enhance the input data in the desired way.

After receiving data from the input devices, the GPDIS 115 will pass that input data to its corresponding Brainwave Enhanced Object. There that data will be modified or merged with the BAP data in the predetermined desired way. As shown in the example of FIG. 5, the joystick fire button and XAxis and the mouse left click button and XAxis are affected.

As an example, in an action game such as QUAKE, one may move forward in a direct relation to the level of concentration. In one example of the present invention, if the player has pushed the joystick forward and is concentrating, they can run very fast through the game, and if they are not concentrating, they will walk very slowly. In this case, the object 230 will form the product of the Joystick's X axis variable, obtained from the of Joystick Input Object 220 and the Attention Indicator variable, which has been increased by a small constant number (such as 0.1) to permit slow movement when concentration has lapsed. If the player did not want to move at all, he would set the Joystick's X axis variable at zero, and no movement would result. However, if the Joystick's X axis variable was not set at zero, but rather at an analog number indicating the player's intent to move at a desired rate, and the Attention Indicator variable was a relatively high number (ranging, for example, up to 10), then the player's game piece would run very quickly through the game.

As a further example, in the same game of QUAKE, it may be desirable to increase the maximum rate of fire of the player's weapon in direct relationship to their level of concentration. With this modification of DirectInput, when the player is concentrating, they can fire their weapon much faster then if they are not concentrating. In this case, the object 230 would be set up to multiply the Joystick's fire button variable by the Attention Indicator variable. If either or both were zero, the weapon would not fire. However, if the Joystick's fire button variable was a binary "one", indicating the player's intent to fire, and the Attention Indicator variable was a number that exceeded a preset threshold, then the player's weapon would fire very frequently. The sensitivity and thresholds of the Attention Indicator could be fixed, configurable by the user, and/or automatically adjusted by an algorithm actuated by software and/or hardware.

The Brainwave Enhanced Mouse Object 330 could be configured in a similar way for enhancing the mouse input with the input from the Attention Indicator to achieve the same desired effects in the same game of QUAKE. Similarly, an object could be configured for any other input device, such as, for example, a head tracker, so this example of FIG. 5 is not limiting the scope of the invention to affecting joystick and/or mouse inputs.

Accordingly, numerous instances of objects may be defined for each individual input device. With specific reference to the headband or headphone input 112, the input object instance 120 will register when the BAP 110 indicates that the user's concentration and/or relaxation has reached a threshold level.

Each object 230, 330 retrieves data from each input object 120, 220, 320 and combines the data therein according to the program. In this manner, joystick and mouse controls are supplemented by the headband input 100. For example, the game program 500 may ordinarily require the user to depress a button located on the joystick to perform a certain action in the computer program, such as a video game. However, by combining the headband input 100 with the joystick input 200, the GPDIS 115 may allow a user to substitute his obtaining a predetermined level of concentration in place of his physically depressing the joystick button, while retaining the other control characteristics of the video game. Integration of the Attention Indicator 112 with input data from the joystick 200 and the mouse 300 permits a user to replace or modify specific controls with brainwave input 100 without requiring a modification to the existing computer program, such as a video game 500. More particularly, the GPDIS 115 exports the object data via a DirectX _Acquire command 420, which receives state and/or trend data from the instances created from the objects 230, 330 through the DirectInputDevice:GetDeviceState and the DirectInputDevice: GetDeviceData commands 430. The process described hereinabove is a continuous one, wherein the current instances of each object are constantly updated with new input values.

Alternatively, the filtering, digitizing, averaging, processing and integrating of the signals described hereinabove may be performed by hard-wired electronic circuitry, rather than by software means as described hereinabove, or by any combination of software and hardware processing. Further, other gaming consoles, such as, for example, Sony PlayStation, Sega Saturn, Nintendo Ultra 64, 300M2, Apple Pippin and various types of arcade games, are within the scope of the present invention.

Figure 6:
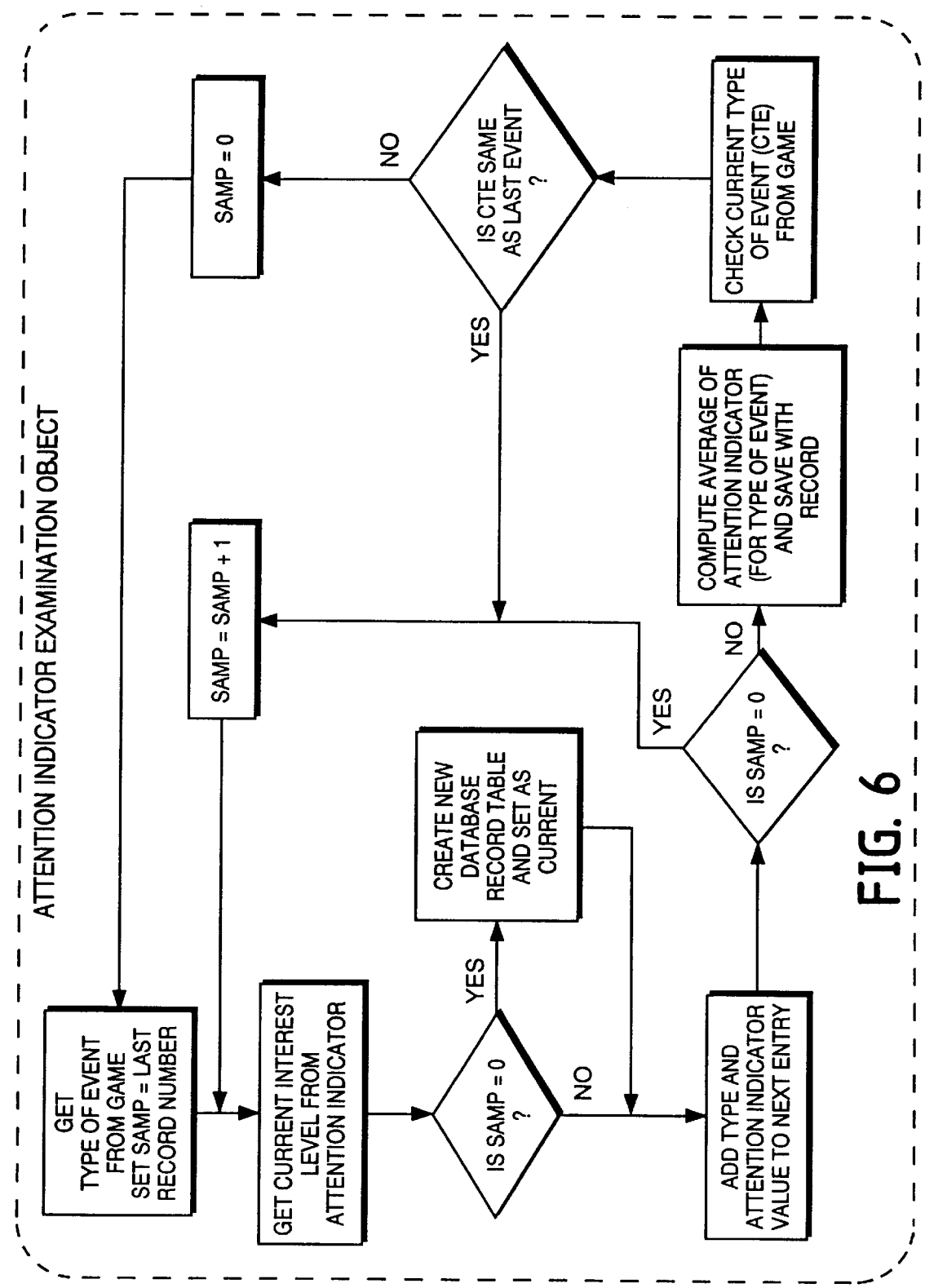
FIG. 6 is a flow chart representation of how the Attention Indicator examination object is sampled and recorded.
Figure 7:
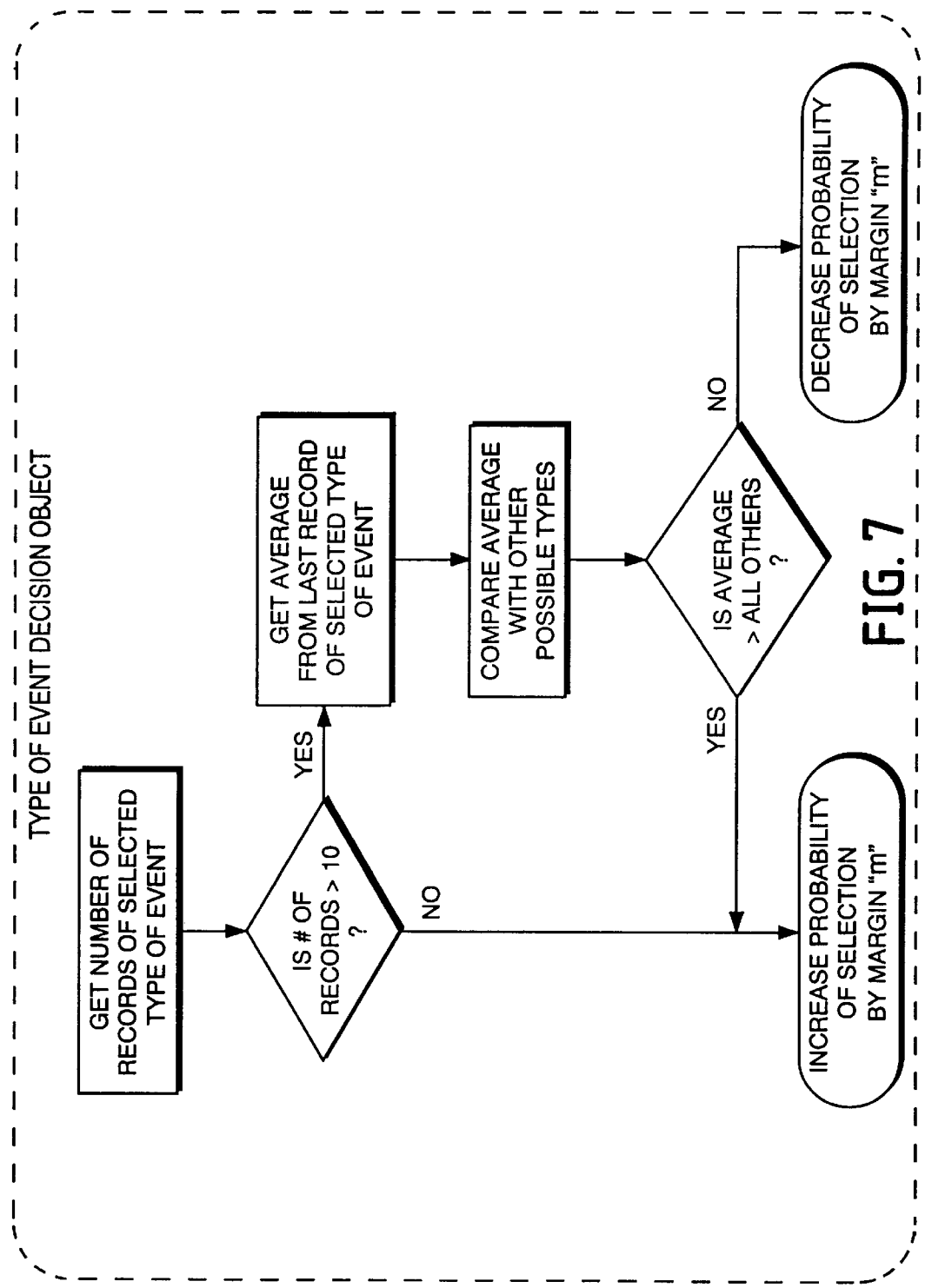
FIG. 7 is a flow chart representation of how the Attention Indicator corresponding to an event can be monitored and compared to that from other events and thereby used to change the probability of future types of events; and, FIG. 8 is a simplified representation of a headphone without electrical connectivity showing the use of two first sensors and two second sensors.

FIGS. 6 and 7 demonstrate the use of artificial intelligence by the system. FIG. 6 demonstrates how the Attention Indicator can be monitored and preferences recorded for later use. For example, player preferences can be recorded and analyzed in order to subsequently affect the current game, to affect the game the next time it is played, or to permit a game developer to subsequently review the player preferences and improve the game by modifying it for future audiences. For example, if, for a portion of the game, the AIndicator is much lower than for other portions, by reviewing the recorded data, the designer could eliminate that portion of the game. Also, this could be programmed into the game. For example, if three paths could be taken and the AIndicator for path 1 is much lower than for paths 2 and 3, the game could change such that only paths 2 and 3 were offered to that player in the future or to other future players.

FIG. 6 details how the previously obtained Attention Indicator 112 can be recorded (by Sample Number) and tabulated in association with the Current Type of Event in the computer program or video game. Subsequently, the average of the Attention Indicator for each Type of Event can be re-calculated.

Similarly, in order to evaluate the user's level of interest in particular experiences during movies, advertisements, educational experiences and other computer programs, the Attention Indicator 112 can be recorded and tabulated in association with the time code of the experience as they are presented to the user. After presenting these experiences to a group of users, the Attention Indicators for each experience can be averaged and statistically analyzed by any known means.

FIG. 7 demonstrates how the game could be modified to suit an individual player's taste or for a certain group of players' tastes. For example, if a specific player has been presented with a choice of weapons in a game and he has typically shown greater interest in a bow and arrow over a bazooka, the game arsenals and ammunition locations can be changed to provide more types of bows than bazookas at arsenals and more choices of arrows than shells at ammunition locations.

As another example, in a football game, a player could be presented with opportunities to pass or to run, and his interest level, as quantitated by the Attention Indicator, could be averaged for each of these choices. Then, during subsequent play, the Type of Event which generated the higher average AIndicator could be presented to that player more frequently. The presentation to that individual or another individual may be by any means, for example, auditory means, visual means, tactile means, olfactory means, gustatory means, or other means.

Finally, while the invention has been described as using a first sensor to measure a frontal lobe brainwave signal and a second sensor to measure a reference signal, then subtracting the reference signal from the frontal lobe brainwave signal to produce a difference signal; any number of first and second sensors can be employed. For example, a pair of first sensors could be positioned at about the hair line and equidistant on opposite sides of a vertical line passing through a wearer's nose. A pair of second sensors could be employed, one engaging each ear lobe. Then, the signals from the first sensors could be mathematically combined and the signals from the second sensors could be mathematically combined to produce a composite frontal lobe signal and a composite reference signal respectively. These composite signals could then be subtracted and processed as before. In the claims, the terms representative frontal lobe brainwave signal and representative reference signal are used. If only one first and second sensor are employed, the representative signals are those obtained by the first and second sensors. If more than one first and second sensors are employed, the representative signals are the composite frontal lobe signal and composite reference signal.

Figure 8:
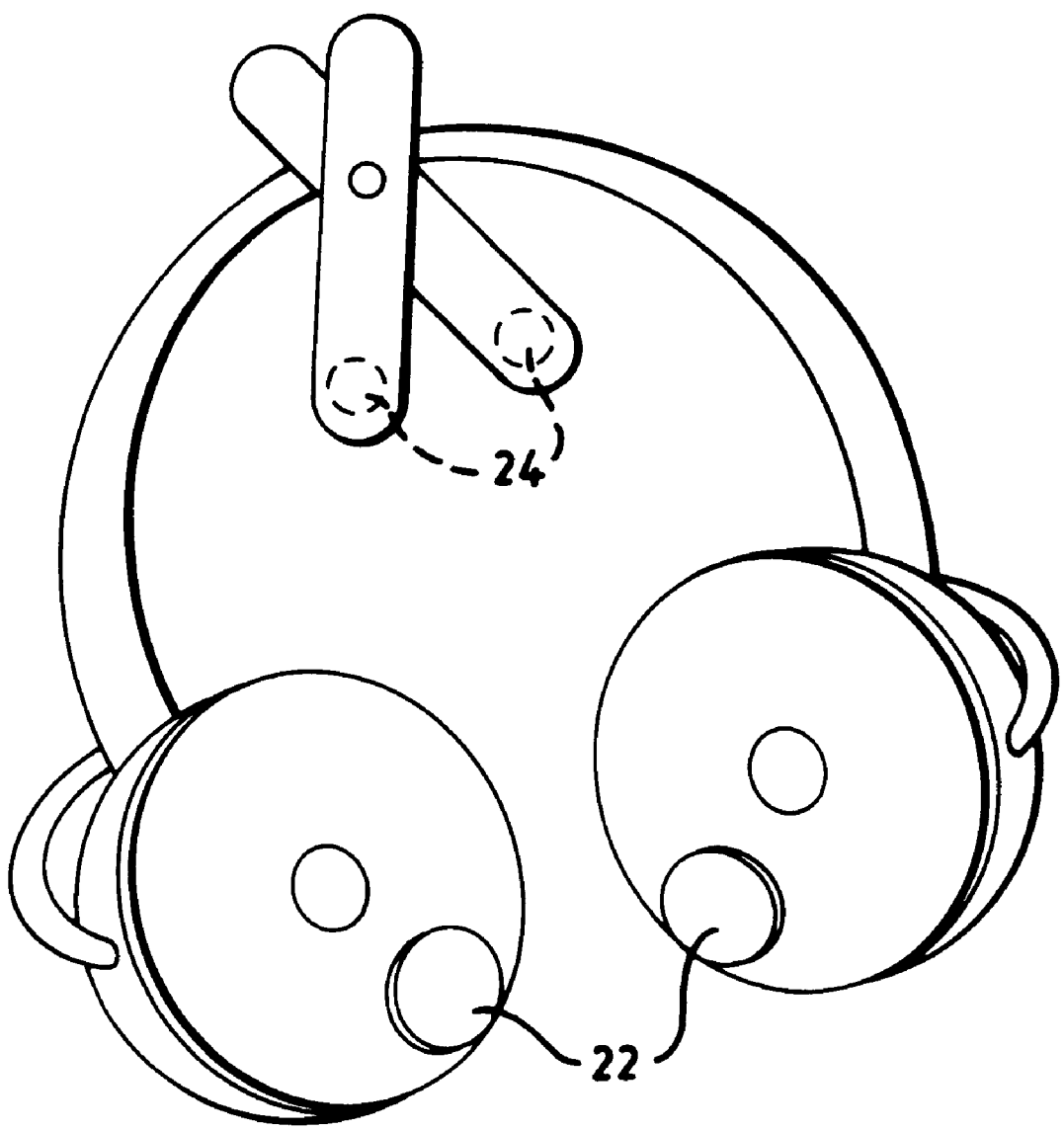

As an example of how this could be accomplished, a simplified representation of a headphone, as previously described, without electrical connectivity being shown, and related to the disclosure in Cowan's 08/590,405 application, is shown in FIG. 8. The headphone includes a pair of first sensors included in frontal lobe sensor units 24, each attached to a flexible and adjustable metal extender. The metal extenders are attached to the headphone headband. Preferably, the sensor units 24 are removably attached, for example, by a hook and loop material, to the extenders so that the sensor units 24 can be adjusted for different wearers of the headphone. This removable attachment also facilitates the wetting of sponges in the sensor units. The headphone also includes a pair of second sensors included in sensor units 22, each of which is received by an ear pad.

Although the present invention has been described in terms of specific embodiments which are set forth in detail, it should be understood that this is by illustration only and that the present invention is not necessarily limited thereto, since alternative embodiments not described in detail herein will become apparent to those skilled in the art in view of the disclosure. Accordingly, modifications are contemplated which can be made without departing from either the spirit or the scope of the present invention as described hereinabove.

We claim:

1. A method for determining an individual's intensity of focused attention, comprising the steps of:

a. obtaining a representative frontal lobe brainwave signal from at least one first sensor in an electrically connective relation to said individual's frontal lobe;

b. obtaining a representative reference signal from at least one second sensor in an electrically connective relation to a more electrically-neutral location;

c. subtracting said representative reference signal from said representative frontal lobe brainwave signal to produce a difference frontal lobe brainwave signal, and processing said difference frontal lobe brainwave signal to produce an AIndicator signal indicative of said individual's intensity of focused attention, where said AIndicator signal is inversely proportional to any mathematical transformation of an amplitude measure of said difference frontal lobe brainwave signal;

d. inputting said AIndicator signal to a device; and, e. repeating steps a–d, as desired.

2. The method of claim 1, where said at least one first sensor obtains said frontal lobe brainwave signal within an area bounded by two lines, each line running between said individual's two earlobes, one line passing through the shallowest portion of the individual's nose called the nasion and the other line passing through a point one inch forward of the highest, most central part of the individual's head called the vertex.

3. The method of claim 2, where said at least one first sensor measures said frontal lobe brainwave signal at a location within two inches either side of a bisector line, said bisector line being transverse to both of said two lines and dividing said area into two equal pieces.

4. The method of claim 3, where said at least one second sensor obtains said representative reference signal from at least one of said individual's earlobes.

5. The method of claim 1, where said AIndicator signal represents an aggregate amplitude level of said difference frontal lobe brainwave signal over a low frequency band.

6. The method of claim 5, where said low frequency band is limited to frequencies of not more than 40 Hertz.

7. The method of claim 1, where said AIndicator signal represents an aggregate power level of said difference frontal lobe brainwave signal over a low frequency band.

8. The method of claim 7, where said low frequency band is limited to frequencies of not more than 40 Hertz.

9. The method of claim 1, where the step of processing said difference frontal lobe brainwave signal includes rejecting eye movement and other artifacts.

10. The method of claim 1, where said device is a computer and where said AIndicator signal inputted thereto is used by a program running on said computer to provide said individual with an indication of said individual's intensity of focused attention.

11. The method of claim 1, where said device is a computer and where said AIndicator signal inputted thereto is used by a program running on said computer to affect said program's execution.

12. The method of claim 11, where said device receives at least one other input signal and where said AIndicator signal supplements an effect of said at least one other input signal.

13. The method of claim 12, where said device receives at least one additional input signal and where said AIndicator signal does not supplement said effect of said at least one additional input signal.

14. The method of claim 11, where said AIndicator signal used by said program affects what is presented to another individual.

15. The method of claim 11, where said AIndicator signal used by said program affects what is presented to said individual.

16. The method of claim 11, further including the step of classifying said individual into a selected class of individuals and using said AIndicator signal from previous individuals in said selected class to affect what is presented to said individual.

17. The method of claim 1, where said device functions as a recorder and where said AIndicator signal is recorded and correlated to at least one event.

18. The method of claim 17, where said AIndicator signal from a plurality of individuals is simultaneously recorded and correlated to at least one event.

19. The method of claim 1, where said at least one first sensor comprises more than one first sensor, and where said representative frontal lobe brainwave signal is a combination of a plurality of frontal lobe brainwave signals, each of said plurality of frontal lobe brainwave signals being obtained from a different one of said at least one first sensor.

20. The method of claim 1, where said at least one second sensor comprises more than one second sensor, and where said representative reference signal is a combination of a plurality of reference signals, each of said plurality of reference signals being obtained from a different one of said at least one second sensor.

21. The method of claim 1, where said first sensor is provided in a flexible holder receivable on said individual's head.

22. The method of claim 21, where said flexible holder further comprises:

a. a flexible band member that can exert pressure to hold said at least one first sensor in electrically connective relation to said individual's head;

b. a first sensor unit attached to said flexible band member, said first sensor unit including a first sponge receiving said first sensor;

c. where said first sensor unit is spaced so that when said flexible holder is placed on said individual's head, said first sensor will be in a first location to obtain said representative frontal lobe brainwave signal.

23. The method of claim 22, where said first sponge has a trapezoidal shaped cross-section having a triangular portion and a rectangular portion, said triangular portion engaging said flexible band member.

24. The method of claim 22, where said first sponge is partly covered by a flexible, electrically-isolating glue compound thereby creating a fluid reservoir.

25. The method of claim 24, where said glue compound is used to attach said first sensor unit to said flexible band member.

26. The method of claim 24, where a hook and loop fastener is used to attach said first sensor unit to said flexible band member.

27. The method of claim 22, where said flexible band member is an elastic band member.

28. The method of claim 21, where said flexible holder is a headphone with at least one extender made of flexible metal attached thereto, said at least one extender having a first sensor unit attached thereto, said first sensor unit including said at least one first sensor, where said first sensor unit is spaced so that when said headphone is placed on said individual's head, said first sensor will be in a first location to measure said frontal lobe brainwave signal.

29. The method of claim 28, where said headphone includes at least one earpiece, said at least one earpiece receiving a second sensor unit, said second sensor unit including said at least one second sensor.

30. A method for using a brainwave signal to affect a program running on a computer, comprising the steps of:

a. providing a sensor to measure a brainwave signal of a user;

b. measuring said brainwave signal with said sensor and processing said brainwave signal to produce a processed signal;

c. inputting said processed signal to said computer, where said computer receives at least one other input signal from at least one other input device d. determining from said signals the interest level of said user at any given time; and, e. modifying said program to present more experiences that are of interest to said user based upon said derermination step.

31. A method for using a brainwave signal to affect a program running on a computer, comprising the steps of:

a. providing a sensor to measure a brainwave signal of a user;

b. measuring said brainwave signal with said sensor and processing said brainwave signal to produce a processed signal;

c. inputting said processed signal to said computer for analysis by said program;

d. determining from said processed signals the interest level of said user for any event generated by said program at an given time; and, e. maintaining a record of events presented to said user and the resulting interest levels of said user to said events.

32. The method of claim 31 further comprising the step of modifying said program to present a greater frequency of those types of events already presented to said user that are of interest to said user based upon said record of events.

* * * * *